(12) United States Patent
Duplan et al.

(10) Patent No.: US 9,566,222 B2
(45) Date of Patent: Feb. 14, 2017

(54) PEPTIDYL ARGININE DEIMINASE 1 AND/OR 3 ACTIVATOR COMPOUNDS IN THE EPIDERMIS AND USES THEREOF

(75) Inventors: Hélène Duplan, Auzeville Tolosane (FR); Sylvie Daunes-Marion, Toulouse (FR); Stéphane Poigny, Saubens (FR); Marie-Claire Mechin, Lapeyrousse-Fossat (FR); Guy Serre, Toulouse (FR); Michel Simon, Belberaud (FR)

(73) Assignee: PIERRE FABRE DERMO-COSMETIQUE, Boulogne-Billancourt (FR)

( * ) Notice: Subject to any disclaimer, the term of this patent is extended or adjusted under 35 U.S.C. 154(b) by 0 days.

(21) Appl. No.: 14/110,977

(22) PCT Filed: Apr. 11, 2012

(86) PCT No.: PCT/EP2012/056596
§ 371 (c)(1),
(2), (4) Date: Oct. 10, 2013

(87) PCT Pub. No.: WO2012/140095
PCT Pub. Date: Oct. 18, 2012

(65) Prior Publication Data
US 2014/0030200 A1     Jan. 30, 2014

(30) Foreign Application Priority Data

Apr. 11, 2011     (FR) ....................................... 11 53135

(51) Int. Cl.
| | |
|---|---|
| A61K 8/49 | (2006.01) |
| A61Q 19/00 | (2006.01) |
| A61K 9/00 | (2006.01) |
| A61K 31/522 | (2006.01) |
| A61K 45/06 | (2006.01) |
| A61K 9/06 | (2006.01) |
| A61Q 1/00 | (2006.01) |
| A61K 47/10 | (2006.01) |
| A61Q 1/02 | (2006.01) |
| A61Q 3/00 | (2006.01) |
| A61Q 5/00 | (2006.01) |

(52) U.S. Cl.
CPC ........... *A61K 8/4953* (2013.01); *A61K 9/0014* (2013.01); *A61K 9/06* (2013.01); *A61K 31/522* (2013.01); *A61K 45/06* (2013.01); *A61K 47/10* (2013.01); *A61Q 1/00* (2013.01); *A61Q 1/02* (2013.01); *A61Q 19/007* (2013.01); *A61K 2800/78* (2013.01); *A61Q 3/00* (2013.01); *A61Q 5/00* (2013.01)

(58) Field of Classification Search
CPC .................................................... A61K 31/522
USPC ......................................................... 424/401
See application file for complete search history.

(56) References Cited

U.S. PATENT DOCUMENTS

| | | | |
|---|---|---|---|
| 5,030,451 A | 7/1991 | Trebosc et al. | |
| 7,604,812 B2 * | 10/2009 | Franke | ................... A61K 8/064 424/401 |
| 2002/0054928 A1 | 5/2002 | Picard-Lesboueyries | |
| 2002/0150597 A1 | 10/2002 | Silva et al. | |

FOREIGN PATENT DOCUMENTS

| | | | | |
|---|---|---|---|---|
| DE | EP 1693071 A2 * | 8/2006 | ............... | A61K 8/64 |
| EP | 1 181 926 A1 | 2/2002 | | |
| FR | 2639541 A1 | 6/1990 | | |
| GB | 2 221 391 A | 2/1990 | | |
| WO | WO 2004/041168 A2 | 5/2004 | | |
| WO | WO 2007/032624 A1 | 3/2007 | | |
| WO | WO 2010/019450 A2 | 2/2010 | | |

OTHER PUBLICATIONS

Poucher's perfumes, cosmetics and soaps, 2000, Kluwer Academic Publishers, (10th ed. By Hilda Butler), pp. 404-405.*
International Search Report for PCT/EP2012/056596 dated May 14, 2012.

* cited by examiner

*Primary Examiner* — Gina Justice
(74) *Attorney, Agent, or Firm* — Birch, Stewart, Kolasch & Birch, LLP (57) ABSTRACT

The present invention relates to the activation of peptidyl arginine deiminase (PADs) 1 and/or 3 in the epidermis by at least one active agent used alone or in combination, namely caffeine, acefylline and/or theobromine in a cosmetic and/or pharmaceutical composition. The present invention also relates to the use of the aforementioned active agents in cosmetics and/or therapeutics, alone or in combination, in order to improve the barrier functions of the epidermis, to prevent and/or treat symptoms related to dry skin or to improve and/or promote hydration of the keratinous layer. Finally, the invention relates to increasing the activity of PAD1 and/or PAD3 in the epidermis.

15 Claims, 7 Drawing Sheets

PEPTIDYL ARGININE DEIMINASE 1 AND/OR 3 ACTIVATOR COMPOUNDS IN THE EPIDERMIS AND USES THEREOF

The present invention relates to the field of molecules capable of activating peptidyl-arginine deiminase type I (or PAD1) and/or peptidyl-arginine deiminase type III (or PAD3) including acefylline or a salt thereof; and to all applications of said molecules in the fields of cosmetics and therapeutics.

More particularly, the present invention relates to the cosmetic use of acefylline or a salt thereof as a moisturizing agent for the skin.

The present invention further relates to the use of a dermatological composition including acefylline or a salt thereof to treat dry skin in the case of skin diseases such as xerosis, ichthyosis, psoriasis, atopic dermatitis, hyperkeratosis, and bullous congenital ichthyosiform erythroderma.

The skin is composed of three compartments, the hypodermis, which is the deepest, the dermis and the epidermis. The latter is a cornified malpighian epithelium which protects the body from mechanical, chemical and biological harm, prevents water loss by limiting evaporation of the water contained in the skin, and participates in photoprotection by adsorbing a portion of ultraviolet rays. These vital functions are collectively called the "epidermal barrier function."

The epidermis is mainly composed of keratinocytes. These proliferate in the basal layer and then undergo a program of vectorized differentiation to constitute successively the spinous and then granular layers. Finally, during cornification, they die and are transformed into corneocytes. The accumulation of corneocytes forms the most external cellular layer of the epidermis, called the horny layer or stratum corneum. The stratum corneum is principally responsible for the epidermal barrier function, due to its mechanical resistance, its water tightness and its content of antimicrobial peptides and urocanic acid.

Corneocytes lack a nucleus and other cellular organelles. They are composed of a fibrous matrix, containing mainly keratins and filaggrin, surrounded by a resistant protein shell that replaces the plasma membrane, the cornified envelope. Corneocytes are connected to each other by novel junction structures, corneodesmosomes. During desquamation, a process that is very finely controlled by numerous proteases and protease inhibitors, the most superficial corneocytes detach from the skin after proteolysis of the corneodesmosomes.

Physiologically, the horny layer contains 10% to 15% of water. This moisturization, which must be maintained whatever the external water conditions, is essential to the epidermal barrier and to desquamation. Indeed, it enables the activity of numerous enzymes, both inside (proteases, transglutaminases, PADs, etc.) and outside (proteases, lipases, glycosidases, etc.) corneocytes. It also has a plasticizing effect that enables the stratum corneum to preserve its elasticity and its integrity after mechanical stress.

A decrease in the moisturization of the horny layer, characteristic of "dry" skin or xerosis, appears as a feeling of tightness, unpleasant to the touch, a scaly appearance and the appearance of persistent superficial cracks and squamae. At the molecular level, it induces a) a decrease in the degradation of desmosomal components (corneodesmosin, desmosomal cadherins, and plaque proteins) and the retention of corneodesmosomes on the entire corneocyte surface and throughout the height of the horny layer, leading to hyperkeratosis and b) changes in the maturation of intercellular lipids and corneal envelopes.

Xerosis can occur on any anatomical region and in highly varied contexts, for example in certain climatic conditions (cold, wind, dryness, rapid and repeated passing from an air-conditioned building where the air is cold and dry to the outside where it is hot and humid), under the effect of psychological stresses and chemical factors (alcohol, organic solvents, detergents, etc.; for example repeated washing with certain soaps) or physical factors (ultraviolet rays). It can also appear in newborns as a consequence of the sudden passing from an aqueous medium—amniotic liquid—to the air, and in the elderly, according to season. But it can also be induced by exposure to the sun.

Many skin diseases also cause a disturbance of the epidermal barrier and dryness of the horny layer: ichthyosis, in particular ichthyosis vulgaris (OMIM 146700), atopic dermatitis (OMIM 605803), psoriasis (OMIM 177900).

Moisturization of the horny layer is ensured by natural moisturizing factor (NMF), which enables the most external layers of corneocytes to retain moisture by opposing the drying action of the environment. The composition of NMF, which can represent up to 20% of the dry weight of the horny layer, is given below:

| | |
|---|---|
| Free amino acids and derivatives | 52.0 |
| (including pyrrolidone carboxylic acid | 12.0) |
| Lactate | 12.0 |
| Sugars, organic acids, peptides | 8.5 |
| Urea | 7.0 |
| Chloride | 6.0 |
| Sodium | 5.0 |
| Potassium | 4.0 |
| Calcium, magnesium, phosphate | 3.5 |
| Ammonia, uric acid, glucosamine | 1.5 |
| Citrate, formate | 0.5 |

More than 50% of these constituents correspond to free amino acids and to certain of their derivatives. In particular, pyrrolidone carboxylic acid, a spontaneous derivative of glutamine which can represent up to 12% of NMF, plays a major hygroscopic role. Urocanic acid, formed from histidine by histidase, absorbs a portion of ultraviolet-B radiation.

All these amino acids arise directly from the degradation of filaggrin, a basic protein 37 kDa in size, synthesized by granular keratinocytes in the form of a large (400 kDa) precursor, profilaggrin. This essential component of keratohyalin granules is formed by repeating 10- to 12-filaggrin subunits (depending on the individual), each 327 amino acids long and bound together by a 7-amino acid binding peptide. During cornification, profilaggrin is cleaved into basic filaggrin subunits. These combine into intermediate keratin filaments (K1 and K10) and facilitate their aggregation and the formation of the intracorneocyte fibrous matrix. Later, in the horny layer, filaggrin is deiminated which leads to its dissociation from the intermediate filaments. It can then be completely degraded by calpain I, caspase 14 and bleomycin hydrolase, thus generating the amino acids constitutive of NMF. The deimination of filaggrin is thus an essential, even limiting, step in the maintenance of moisturization of the horny layer and of the epidermal barrier function.

Deimination, or citrullination, is a posttranslational modification catalyzed by a family of calcium-dependent enzymes, PADS (E.C.3.5.3.15). It involves the transformation of arginyl residues (positively charged) into citrullyl residues (neutral). There are five PAD isotypes, coded by five distinct genes (called PADI), grouped on the short arm of human chromosome 1 at locus 1p35-36. They are PAD1, PAD2, PAD3, PAD4 and PAD6. Whereas PAD2 is ubiquitous, the other isotypes are expressed in a more restricted manner depending on the tissue analyzed. In particular, only PAD1, PAD2 and PAD3 are detected in normal human epidermis. On the basis of biochemical and physicochemical arguments, and because they are colocalized with filaggrin in the intracorneocyte fibrous matrix, it has been shown that PAD1 and PAD3 are the isotypes responsible for the deimination of filaggrin. It is thus these isotypes which must be targeted if one wishes to act on the production of NMF amino acids.

Furthermore, NMF production is regulated via the catabolism of filaggrin, as a function of external moisture level, according to an adaptive mechanism. For example, during the final days of the embryonic development of the rat, filaggrin accumulates throughout the height of the horny layer. A few hours after birth, it is proteolyzed in the external portion, according to a profile identical to that observed in the skin of adults. Maintaining newborn rats in relative humidity greater than 80% prevents the activation of this degradation process, without bringing into play the synthesis of the protein. Similarly, the level of free amino acids and conductance to the surface of the skin (reflecting moisturization) are restored in 3 days when hairless mice are transferred from a humid environment to a normal environment.

To reduce dry skin, to improve the moisturization of the horny layer and to treat xerosis or ichthyosis, topical applications on the skin of cosmetic or pharmaceutical formulations containing hygroscopic active agents are used. These formulations contain, for example, urea or lactic acid, other components of NMF. Generally, hydroxy acids have become one of the largest classes of compounds for the cosmetics industry, because of their moisturizing and "anti-aging" properties, but the most popular and most commonly used moisturizer is certainly glycerol.

Whatever the formulations already developed, it is obviously necessary to propose new active agents useful for the cosmetics industry and/or the pharmacopeia in order to improve the symptoms of dry skin. The goal of the present invention is precisely to promote the production of NMF by using new compounds capable of acting on PAD1 and PAD3 in order to promote the natural moisturization of the horny layer. This can find a particularly advantageous application in the field of care and/or makeup products for the skin of the body or face, the lips, lashes, eyebrows, hair, scalp or nails; of a sun or self-tanning product; of a hair product notably for coloring, conditioning and/or care of the hair.

Indeed, after significant research, the Applicant discovered in a surprising and unexpected manner that acefylline or a salt thereof, caffeine and theobromine, used alone or in combination, has the capacity to increase the activity of PAD1 and/or PAD3, in particular their capacity to deiminate their physiological substrate, filaggrin, in order to promote the natural moisturization of the horny layer. The chemical formula of these molecules is specified below:

Acefylline
2-(1,3-dimethyl-2,6-dioxo-2,3-dihydro-1H-purin-7(6H)-yl)acetic acid

Caffeine
1,3,7-trimethyl-1H-purine-2,6(3H,7H)-dione

Theobromine
3,7-dimethyl-1H-purine-2,6(3H,7H)-dione

It has been suggested that the deimination reaction is divided into 5 sequential steps:
i) nucleophilic attacks on C$\zeta$ of peptidyl-L-arginine by the thiol group of the Cys of the active site of the enzyme;
ii) formation of hydrogen and saline bonds between the Asp of the active site and the substrate;
iii) cleaving of the bond between the C$\zeta$ and N$\eta$2 of peptidyl-L-arginine and the release of ammonia;
iv) second nucleophilic attack, this time by a water molecule; and
v) hydrolysis of the adduct formed at the conclusion of the preceding reaction and release of the final deimination product, peptidyl-L-citrulline.

Thus, the present invention relates to the activation, by the active agents described above, used alone or in combination, of one or the other of these 5 steps of the reaction catalyzed by PAD1 or PAD3.

Several pathologies are characterized on the clinical level by a deficiency of deimination, such as psoriasis and bullous congenital ichthyosiform erythroderma (OMIM 113800). Similarly, we noted a decrease in the detection of deiminated proteins in the horny layer of patients suffering from atopic dermatitis (see example 3 below). However, in the stratum corneum of patients suffering from psoriasis such as atopic dermatitis, PADs are expressed at a level similar to that of controls, in areas both with lesions and without lesions.

The present invention thus relates to the cosmetic use of a composition including a PAD1 and/or PAD3 activator compound selected from acefylline or a salt thereof, caffeine, theobromine and mixtures thereof as a moisturizing agent for the skin.

More particularly, said composition is intended to promote the deimination of filaggrin in the epidermis.

The composition according to the present invention is also intended to promote the production of NMF (natural moisturizing factor) in the horny layer.

These PAD1 and/or PAD3 activators were thus selected to promote the production of NMF in the horny layer as well as for their use in the moisturization of the epidermis, in particular the horny layer, in the improvement of any form of dry skin, or in the strengthening of the epidermal barrier function and in the prevention of signs of aging skin.

The active agents of the invention can be of any origin, namely isolated from plants such as the coffee tree or cocoa tree, produced by microorganisms even if they are not produced naturally by said organisms of any origin, or obtained by chemical synthesis.

In the context of the invention, the expression "acefylline salts" refers to organic or inorganic acefylline salts.

As organic salts that can be used according to the invention, mention may be made of those described in the prior art FR 2 639 541. Preferably, it will be triethanolamine salt.

As inorganic acefylline salts, mention may be made of sodium, potassium or lithium salts.

In a particular embodiment of the invention, acefylline salt is formed by the addition in the composition including acefylline of an organic or inorganic base as a neutralizing agent. Preferably, the organic base is triethanolamine and the inorganic base is NaOH.

The invention also relates to pharmaceutical and/or cosmetic compositions containing at least one such PAD1 and/or PAD3 activator such as defined above and in particular acefylline or a salt thereof, alone or combined with caffeine and/or theobromine, in combination with at least one pharmaceutically or cosmetically acceptable excipient.

This composition could be preferentially of natural or synthetic origin, more preferentially synthetic.

Preferably, the acefylline present in the composition will represent between 0.5% and 3% by weight of the total weight of the composition in the case of a pharmaceutical composition and between 0.1% and 1% by weight of the total weight of the composition in the case of a cosmetic composition.

Preferentially, the PAD1 and/or PAD3 activator compound used will be acefylline or a salt thereof.

In a particular embodiment of the invention, acefylline or a salt thereof is combined with caffeine and/or theobromine.

Acefylline or a salt thereof, given its activator effect on PAD1 and/or PAD3 enzymes, will enable an increase in the degradation of filaggrin within the horny layer and thus the production of the amino acids comprising NMF, in particular glutamine-derived pyrrolidone carboxylic acid (PCA). An increase in the assayed quantity of this acid shows the moisturizing activity of these compounds.

Preferably, the compositions according to the invention will be administered topically.

Preferably, the composition according to the invention will include at least one liquid fatty phase, which can include at least one compound selected from oils and/or solvents of mineral, animal, plant or synthetic origin, containing carbon, hydrocarbon, fluorine and/or silicone, volatile or non-volatile, alone or in mixture.

In a preferred embodiment, the composition according to the invention will preferentially be provided in the form of a care and/or makeup product for the skin of the body or face, the lips, lashes, eyebrows, hair, scalp or nails; a sun or self-tanning product; a hair product notably for coloring, conditioning and/or care of the hair.

Another aspect of the present invention thus relates to the therapeutic use of the active agents described above, used alone or in combination, to prevent and/or treat these deimination anomalies and/or to promote the moisturization of the horny layer and to improve the symptoms of any form of dry skin pathology.

In the context of the present invention, "dry skin pathology" refers to any type of dry skin, either directly related to skin pathology or resulting from the dermatological treatment of the latter.

In a particular embodiment of the invention, caffeine will be used as the sole therapeutic active ingredient in the composition.

In another preferred embodiment of the invention, theobromine will be used as the sole therapeutic active ingredient in the composition.

The composition according to the invention will enable the moisturization of the skin, in particular the horny layer; to improve any form of dry skin; to strengthen the epidermal barrier function and to prevent the signs of aging skin.

Moisturization of the skin refers to improvement in or maintenance of the water balance of the epidermis.

Improvement in any form of dry skin refers to any improvement in the moisturization of the epidermis, notably characterized by a lack of water in the horny layer, a hydrolipidic film located on the surface which is too thin and which no longer protects the skin, a lack of sebum.

Aging skin refers to, in addition to the effects on the dermis and the loss of tissue elasticity, a weakening of the barrier function. Despite an imperceptible loss of water which increases little, clinical experience has shown that the elderly suffer from dry skin more often than younger people in good health. Firstly, this is explained by a change in the lipid barrier. The epidermal barrier is also more easily altered and slower to be repaired. The Raman spectroscopy technique has made it possible to show that the ability of the stratum corneum to retain water and the quantity of NMF decrease with age, mainly in the most superficial layers.

Ultraviolet B rays are one of the principal causes of the occurrence of skin cancers because of the damage to DNA which they induce, and hence their significant mutagenic capacity. A large portion of them are absorbed by melanin, but the first photoprotective barrier is ensured by a component of NMF, trans-urocanic acid, whose average level is about 5 $\mu g/cm^2$ of skin. This is a relatively effective natural sunscreen which was added to numerous cosmetic products in the 1970s and 1980s. In the stratum corneum, trans-urocanic acid is derived, like most NMF amino acids, from the catabolism of filaggrin.

The present invention thus also relates to the cosmetic use of the active agents described above, used alone or in combination, for the moisturization of the epidermis in order to promote the natural production of trans-urocanic acid and to protect the skin from ultraviolet rays.

The present invention preferentially relates to a composition for use in the treatment and prevention of skin disorders; in the treatment of xerosis, ichthyosis, psoriasis, atopic dermatitis, hyperkeratosis, and bullous congenital ichthyosiform erythroderma.

In a particular embodiment of the invention, the pharmaceutical composition according to the invention contains at least one PAD1 and/or PAD3 activator compound composed of acefylline or a salt thereof in combination with caffeine and/or theobromine and at least one acceptable pharmaceutical or cosmetic excipient, for therapeutic use in the treatment and prevention of skin disorders; in the treatment of xerosis, ichthyosis, hyperkeratosis, and bullous congenital ichthyosiform erythroderma.

The present invention also relates to a method of cosmetic treatment of keratinous material, notably the skin of the body or face, the lips, nails, hair and/or lashes, comprising the application on said material of a cosmetic composition according to the invention.

In the context of the present invention, various biochemical analysis methods have made it possible to select several molecules that modulate the catalytic activity of PAD1 and PAD3 in view of their particular ability to deiminate filaggrin. These results are illustrated on the appended drawings which represent.

After purification, PAD1, PAD3 and recombinant human filaggrin (Fil-His) were separated by polyacrylamide gel electrophoresis in the presence of SDS (SDS-PAGE), stained with Coomassie blue or immunodetected, as indicated. AHF11, an anti-filaggrin monoclonal antibody, detects non-deiminated Fil-His of about 45 kDa. Apparent molecular masses are indicated at left in kDa.

After incubation with PAD1, Fil-His was immunodetected by AHF11, an anti-filaggrin monoclonal antibody. Apparent molecular mass is indicated at left in kDa and incubation times are indicated in minutes (min) at the top of the illustration. It is noted that the deimination of Fil-His by PAD1 induces a progressive change in its migration from 45 toward 66 kDa.

After incubation with PAD1, in the presence of 5 mM streptomycin (str) or in the presence of 1% dimethylsulfoxide (d), the solvent, Fil-His was immunodetected by AHF11, an anti-filaggrin monoclonal antibody, or by AMC, an anti-citrulline antibody, as indicated. Apparent molecular masses are indicated at left in kDa and incubation times are indicated in minutes (min) at the top of the illustration. It is noted that PAD1 is inhibited by streptomycin since the immunodetection intensity by AMC is lower when incubation takes place in the presence of this molecule in comparison with an incubation carried out in the presence of solvent alone.

After incubation with PAD1, in the presence of 50 μM caffeine (caf) or in the presence of 1% dimethylsulfoxide (d), the solvent, Fil-His was immunodetected by AHF11, an anti-filaggrin monoclonal antibody, or AMC, an anti-citrulline antibody, as indicated. Apparent molecular masses are indicated at left in kDa and incubation times are indicated in minutes (min) at the top of the illustration. It is noted that PAD1 is activated by caffeine since Fil-His is more strongly deiminated in the presence of this molecule than in the presence of solvent alone.

After incubation with PAD3, in the presence of 200 μM theobromine (theo) or in the presence of 1% dimethylsulfoxide (d), the solvent, Fil-His was immunodetected by AHF11, an anti-filaggrin monoclonal antibody, or AMC, an anti-citrulline antibody, as indicated. Apparent molecular masses are indicated at left in kDa and incubation times are indicated in minutes (min) at the top of the illustration. It is noted that PAD3 is activated by theobromine.

After incubation with PAD3, in the presence of acefylline (ace) in a final concentration of 50 μM (top) or 200 μM (bottom), or in the presence of 1% dimethylsulfoxide (d), the solvent, Fil-His was immunodetected by AHF11, an anti-filaggrin monoclonal antibody, or AMC, an anti-citrulline antibody, as indicated. Apparent molecular masses are indicated at left in kDa and incubation times are indicated in minutes (min) at the top of the illustrations. It is noted that PAD3 is activated by acefylline (particularly visible at the highest concentration).

Fil-His was incubated in the presence of PAD1 for 5 minutes (A-B) or in the presence of PAD3 for 60 minutes (C-D). Before incubation, 312.5 μM caffeine (Caf), acefylline (Ace) or theobromine (Theo) was added to the reaction mixture, alone (A and C) or in combination (B and D), as indicated. After incubation, Fil-His was immunodetected by anti-citrulline antibody (AMC) and the immunodetection intensity was quantified using the ImageJ software. The data are presented in the form of histograms as a relative percentage of the activity of each enzyme in comparison with the controls (−) carried out in the absence of active agent.

Deiminated proteins were immunodetected by anti-citrulline (AMC) after chemical modification of the citrullines. The negative control (Neg) was carried out in parallel. PAD1 and PAD3 were immunodetected by anti-PAD 1 and anti-PAD3 antibodies as described above (example 3). Images representative of the results obtained for eight patients (DA1, 2 and 3) and three controls (Nor1) are presented [bar=150 μm].

Reconstructed epidermises were treated topically for 24 hours with a control gel (1) or a gel containing acefylline at a concentration of 3% (2 and 3) in the form of triethanolamine salts (2) or sodium salts (3).

A. Total proteins were separated by electrophoresis and immunodetected by the anti-citrulline antibody (AMC) and an anti-actin antibody. The experiment was carried out in triplicate (I, II and III). Apparent molecular masses are indicated at left in kDa.

B. The immunodetection intensity was quantified using the ImageJ software. The values obtained were normalized in relation to actin. They are presented in the form of histograms as a relative percentage in comparison with the controls carried out in absence of acefylline.

It is noted that, in comparison with the epidermises treated with the control gel, the immunodetection intensity of the citrullinated proteins is greater for the epidermises treated with the gel containing acefylline in salt form.

Cryosections of untreated normal skin (A and D) and reconstructed epidermises treated topically for 24 hours with a control gel (B and E) or a gel containing acefylline at a concentration of 3% in the form of sodium salts (C and F) were analyzed immunohistologically with anti-citrulline antibody (AMC) with (A-C) or without (D-F; negative controls) modification of the citrullines [bar=150 μm]. One notes an increase in the intensity of staining of the horny layer of the reconstructed epidermis treated with acefylline in the form of sodium salt (C) in comparison with the reconstructed epidermis treated with the control gel (B).

Pharmacological Evaluation

A/ Measurement of PAD1 and/or PAD3 Activity Using Recombinant Human Filaggrin

Methods:

1. Production and Purification of Recombinant Human Filaggrin

A 324-amino acid subunit of recombinant human filaggrin ("GenBank" database accession number: AF043380) was produced by fusion with a 6-histidine label at the COOH-terminus using the pET-41b vector (Merck, KGaA, Darmstardt, Germany) in the *Escherichia coli* BL21 Codon plus (DE3+)-RIL strain (Stratagene, La Jolla, Calif.).

To this end, the cDNA was first amplified by PCR using the following oligonucleotide pair:
5'-CATATGCTATACCAGGTGAGCACTCATG-3' and
5'-CTCGAGCCCTGAACGTCCAGACCGTCC-3',
from mRNA extracted from human epidermis, and then purified and cloned into the pCRII-Topo vector (Invitrogen, Carlsbad, Calif.).

The PCR product was thus flanked by a NdeI site and a XhoI site, these two additional restriction sites enabling subcloning from the pCRII-Topo vector to the pET-41b expression vector. After verification by sequencing, the filaggrin subunit, hereafter called Fil-His, was produced and purified by nickel affinity chromatography according to a protocol well-known to persons skilled in the art. The Fil-His recombinant protein thus purified was analyzed by SDS-PAGE (10% gel) and immunodetected by AHF11 anti-filaggrin monoclonal antibody. The degree of purity was monitored by staining with Coomassie blue, the Fil-His protein having an apparent molecular weight of about 45 kDa (see FIG. 1). The concentration of the purified fraction obtained was measured (in mg/ml) with a NanoDrop 1000 (Fisher Scientific, Illkirch, France) using a standard range of bovine serum albumin.

2. Production of Active Recombinant Human PAD1 and PAD3

The PAD1 and PAD3 produced and purified according to protocols well-known to persons skilled in the art were purchased from Professor Hidenari Takahara (University of Ibaraki, Japan). The characteristics of said purified active recombinant human PAD1 and PAD3 are presented in the following table:

| PAD | Activity* (units/ml) | Protein concentration (mg/ml) | Specific activity (units/mg) |
|---|---|---|---|
| PAD1 | 206.0 | 0.696 | 296.0 |
| PAD3 | 10.2 | 0.400 | 25.5 |

*a unit is defined as the quantity of PAD that catalyzes the formation of 1 μmol of Bz-L-CiT-O—Et from Bz-L-Arg-O—Et in 1 hour at 55° C.

Figure 1:
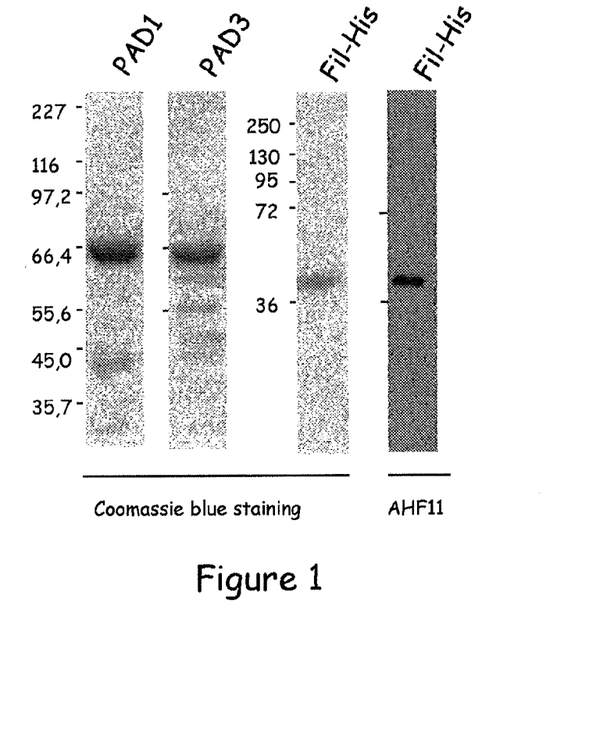
FIG. 1: Analysis of purified recombinant proteins.

The degree of purity of each enzyme was evaluated by staining with Coomassie blue after separation by SDS-PAGE (see FIG. 1).

3. Deimination of Fil-his by PAD1 and PAD3

25 ng of Fil-His was incubated at 50° C. in the presence of 40 mU of PAD1 or PAD3 in deimination buffer (10 mM $CaCl_2$, 5 mM dithiothreitol, 50 mM Tris-HCl pH 7.4). After a variable incubation period according to the PAD isoform (generally 2 to 5 minutes for PAD1 and 60 to 180 minutes for PAD3), the reaction was quenched by adding sample buffer. The proteins were then separated by SDS-PAGE and immunodetected by AHF11 anti-filaggrin monoclonal antibody and AMC modified anti-citrulline antibody (Millipore, Mollsheim, France) diluted to 1/5000.

Results:

1. Evaluation of the Deimination of Fil-his

Figure 2:
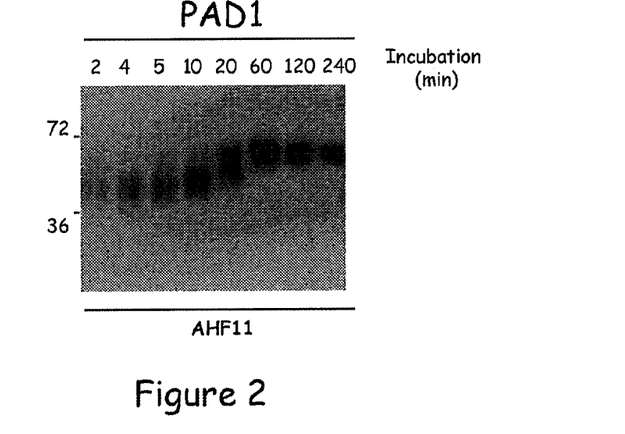
FIG. 2: Kinetics of the deimination of recombinant human filaggrin (Fil-His) by PAD1.

When Fil-His is not deiminated its apparent molecular mass in denaturing gel is about 45 kDa. It migrates in the form of a single protein band after staining with Coomassie blue or immunodetection with AHF11 antibody (see FIG. 1). The deimination of Fil-H is induces a progressive increase in its apparent molecular mass from 45 to ~66 kDa (see FIG. 2). The ~66 kDa form corresponds to the completely deiminated form, with the intermediate forms corresponding to the more or less deiminated forms. The degree of deimination of Fil-His is thus correlated to its apparent molecular mass after separation by SDS-PAGE.

Figure 3:
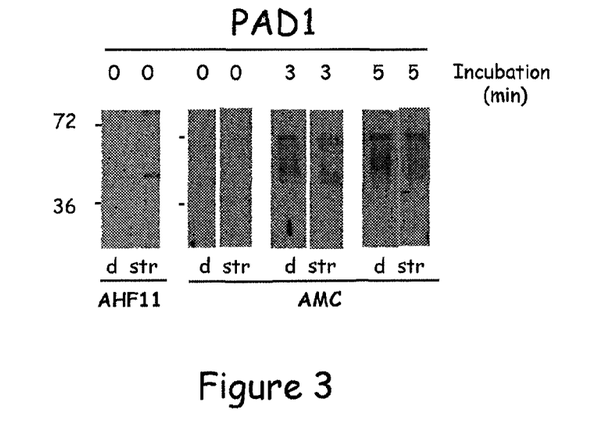
FIG. 3: Deimination of recombinant human filaggrin (Fil-His) by PAD1 in the presence or absence of streptomycin.

Fil-His is immunodetected by AMC antibody only after incubation with an active PAD. The immunodetection intensity is greater the more highly it is deiminated (see FIG. 3).

2. Streptomycin Inhibits PAD1

A change in filaggrin migration and/or a change in immunodetection intensity by the AMC antibody makes it possible to evaluate the effect (activator or inhibitor) on PADS by a molecule added to the reaction mixture before the start of the deimination reaction. Inhibition of PAD1 by streptomycin, for example, can be demonstrated by this method (see FIG. 3). The immunodetection intensity by AMC antibody of the bands whose mass is either ~66 kDa, or between 45 and ~60 kDa, is lower when Fil-His is incubated for 3 or 5 minutes with PAD1 in the presence of 5 mM streptomycin, in comparison with incubation at all identical points, in the presence of solvent alone (1% dimethylsulfoxide).

B/ PAD1 and/or PAD3 Activators

Method:

Deimination of Fil-his by PAD1 or PAD3 in the Presence of an Active Agent or a Combination of Active Agents The deimination of Fil-His (25 ng) was carried out as described above (paragraph A.3), in deimination buffer (10 mM $CaCl_2$, 5 mM dithiothreitol, 50 mM Tris-HCl pH 7.4) at 50° C. in the presence of 40 mU of PAD1 or PAD3, for 0, 3, 5, 60 and 180 minutes. The active agent in solution in 1% dimethylsulfoxide to obtain a final concentration of 50, 200 and 312.5 μM, or 1% dimethylsulfoxide alone (control) or a mixture of several active agents each diluted to 312.5 μM in 1% dimethylsulfoxide was added to the reaction mixture before adding the enzyme. In certain cases, the active agents were diluted in water. After incubation, the proteins of the reaction mixture were immunodetected by AMC antibody. The immunodetection intensity was quantified by densitometry with the NIH ImageJ software.

Results:

1. Activation of PAD1 by Caffeine

Figure 4:
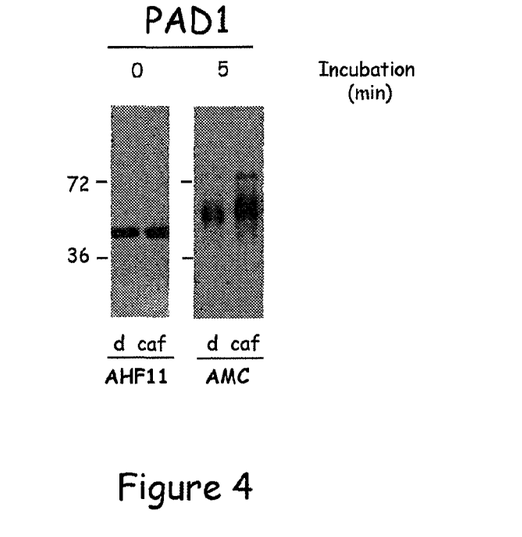
FIG. 4: Deimination of recombinant human filaggrin (Fil-His) by PAD1 in the presence or absence of caffeine.

Before deimination, Fil-His is immunodetected by AHF11 antibody as a band of about 45 kDa but is not detected by AMC antibody (see FIG. 4). After 3 and 5 minutes of incubation in the presence of PAD1 and dimethylsulfoxide (1% final), Fil-His is partially deiminated by PAD1: it is then immunodetected by AMC antibody as a wide band between 45 and ~60 kDa in size. After 3 and 5 minutes of incubation in the presence of PAD1 and caffeine (50 µM final in 1% dimethylsulfoxide), the immunodetection intensity of this wide band is greater and an additional band, migrating toward 66 kDa, is detected by AMC antibody (see FIG. 4). This ~66 kDa protein corresponds to completely deiminated Fil-His. A quantitative analysis confirmed this result and showed an increase of 151% in the immunodetection intensity of the bands between 45 and ~66 kDa after incubation in the presence of caffeine, in comparison with the control.

Comparable results were obtained during tests carried out with caffeine solubilized and diluted in ultrapure water.

Caffeine thus activates PAD1.

2. Activation of PAD3 by Theobromine

Figure 5:
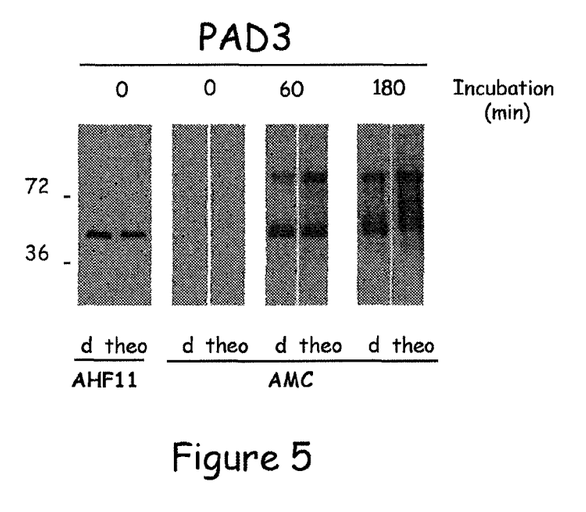
FIG. 5: Deimination of recombinant human filaggrin (Fil-His) by PAD3 in the presence or absence of theobromine.

Before deimination, Fil-His has an apparent mass of about 45 kDa; it is immunodetected by the AHF11 antibody but not by the AMC antibody (see FIG. 5). After 180 minutes of incubation in the presence of PAD3 and dimethylsulfoxide (1%), it is partially deiminated by PAD3: it is then immunodetected by the AMC antibody as a wide band between 45 and ~66 kDa in size. After 180 minutes of incubation in the presence of PAD3 and theobromine (200 µM in 1% dimethylsulfoxide), the intensity of the bands immunodetected by the AMC antibody is greater (see FIG. 5). Quantification of the immunodetection intensity showed an increase of 182%.

Comparable results were obtained during tests carried out with theobromine solubilized and diluted in ultrapure water.

Theobromine thus activates PAD3.

3. Activation of PAD3 by Acefylline

Figure 6:
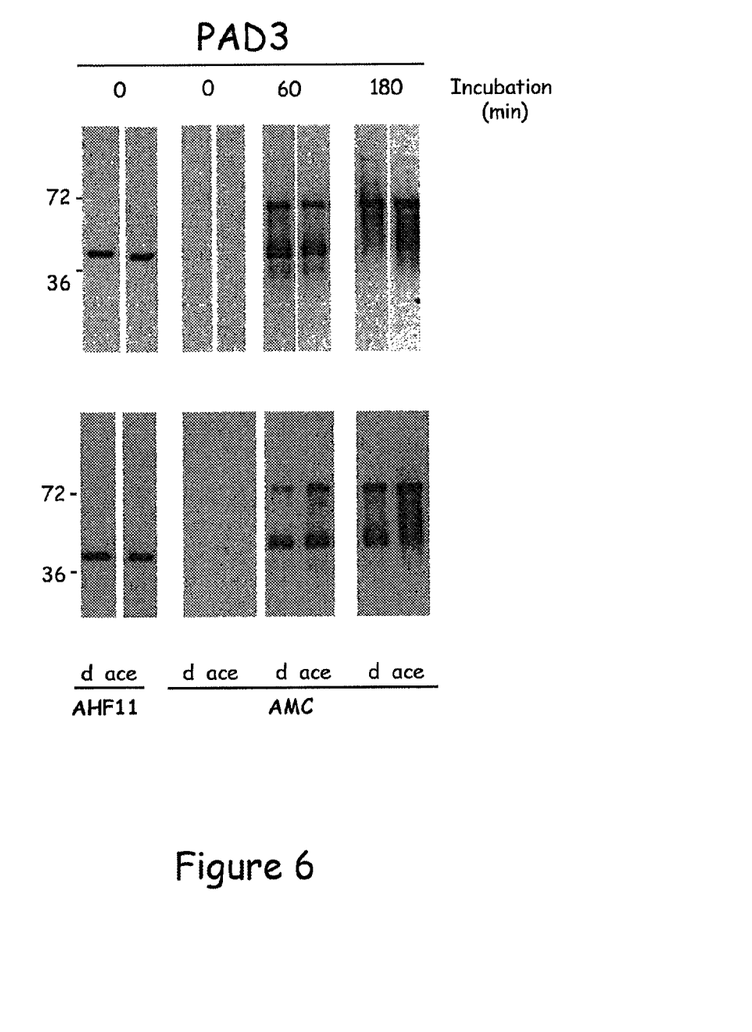
FIG. 6: Deimination of recombinant human filaggrin (Fil-His) by PAD3 in the presence or absence of acefylline.

Before deimination, Fil-His is immunodetected by AHF11 antibody toward 45 kDa but is not detected by AMC antibody (see FIG. 6). After 180 minutes of incubation in the presence of PAD3 and dimethylsulfoxide (1%), Fil-His is partially deiminated by PAD1: it is then immunodetected by AMC antibody as a wide band between 45 and ~60 kDa in size and a band of ~66 kDa. After 180 minutes of incubation in the presence of PAD3 and acefylline (200 µM in 1% dimethylsulfoxide), the intensity of the bands immunodetected by AMC antibody is clearly more intense (see FIG. 6). Quantification of the immunodetection intensity confirmed this result and showed an increase of 225%.

Comparable results were obtained during tests carried out with acefylline solubilized and diluted in ultrapure water.

Acefylline thus activates PAD3.

Figure 7:
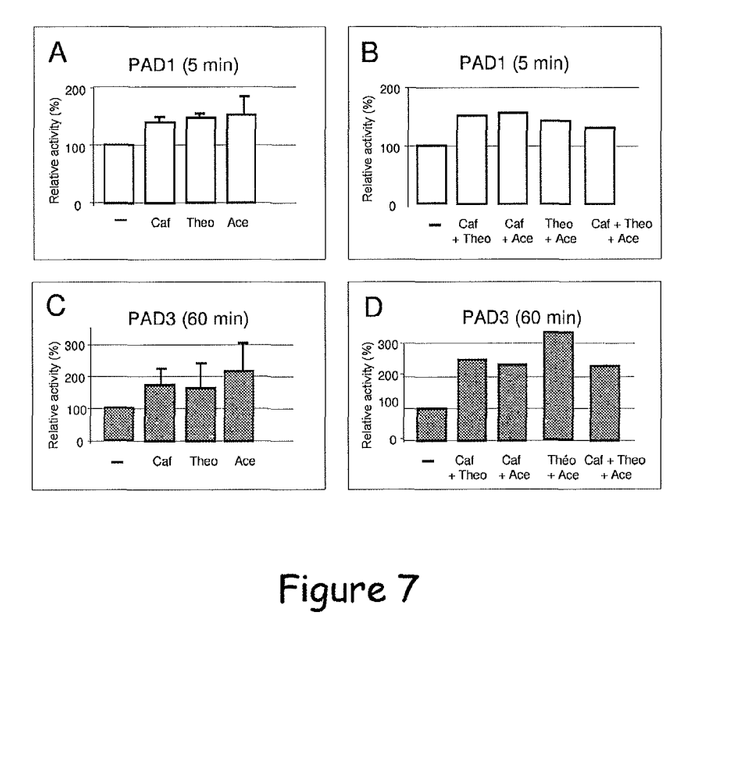
FIG. 7: Deimination of recombinant human filaggrin by PAD1 or PAD3 in the presence of caffeine, theobromine and/or acefylline, alone or in combination.

4. Evaluation of the Effect of a Mixture of Caffeine, Theobromine and/or Acefylline on PAD1 and PAD3 Activity Similar tests of Fil-His deimination by PAD1 (5 minute incubations) and PAD3 (60 minute incubations) were carried out in the presence of each of the three active agents (caffeine, theobromine and acefylline) or a mixture of two or three of these active agents. The active agents were solubilized and then diluted in ultrapure water. They were used at a final concentration of 312.5 µM in the test. The immunodetection intensity by AMC antibody was quantified as before (see FIG. 7).

The results obtained confirmed the activation of PAD1 by caffeine and that of PAD3 by theobromine and acefylline. Furthermore, they demonstrated that the three active agents used individually activate PAD1 and PAD3, with comparable levels of activation (see FIGS. 7A and 7C).

The addition of the active agents in pairs or the three together did not induce an inhibitory effect. The same level of activation of PAD1 was observed (see FIG. 7B). The addition of two or three active agents even seems to activate PAD3 more markedly (see FIG. 7D).

Caffeine, theobromine and acefylline used alone or in combination thus activate PAD1 and PAD3.

C/ Reduction in the Detection of Deiminated Proteins of the Horny Layer of Lesioned Epidermis of the Skin of Patients Suffering from Atopic Dermatitis Methods:

1. Skin Sections

Biopsies 3 mm in diameter were performed on lesioned skin of 8 patients suffering from atopic dermatitis (diagnosis by a doctor of the dermatology department of Toulouse hospital) and on healthy skin of 3 controls, fixed in formol and enclosed in paraffin. Serial sections (6 µm) were made for each biopsy, deposited on Superfrost slides, deparaffinized by successive xylene and ethanol baths and then rehydrated and stained with hematoxylin-eosin or analyzed by immunohistology.

2. Detection of Deiminated Proteins by Immunohistology

To immunodetect deiminated proteins, the skin sections were incubated for 3 hours at 37° C. in modification buffer: 0.0125% $FeCl_3$, 2.3 M $H_2SO_4$, 1.5 M $H_3PO_4$, 0.25% diacetyl monoxime and 0.125% antipyrine. Negative controls were prepared systematically by omitting diacetyl monoxime and antipyrine. After washing with water, the sections were incubated with AMC reference antibody diluted to 1/500 and then developed with the "Impress Reagent anti rabbit Ig PO" kit according to the manufacturer's instructions (Vector Laboratories, Burlingame, Calif.) in the presence of diaminobenzidine as the chromogenic substrate of peroxidase. Finally, counter-staining was carried out with hematoxylin.

3. Detection of PAD1 and PAD3 by Immunohistology

PAD1 and PAD3 were immunodetected using specific anti-PAD1 and anti-PAD3 (B3) anti-peptide antibodies diluted to 1/80 and 1/100, respectively, according to the protocol described above. Counter-staining was carried out with hematoxylin. Negative controls were prepared by omitting the primary antibody.

Figure 8:
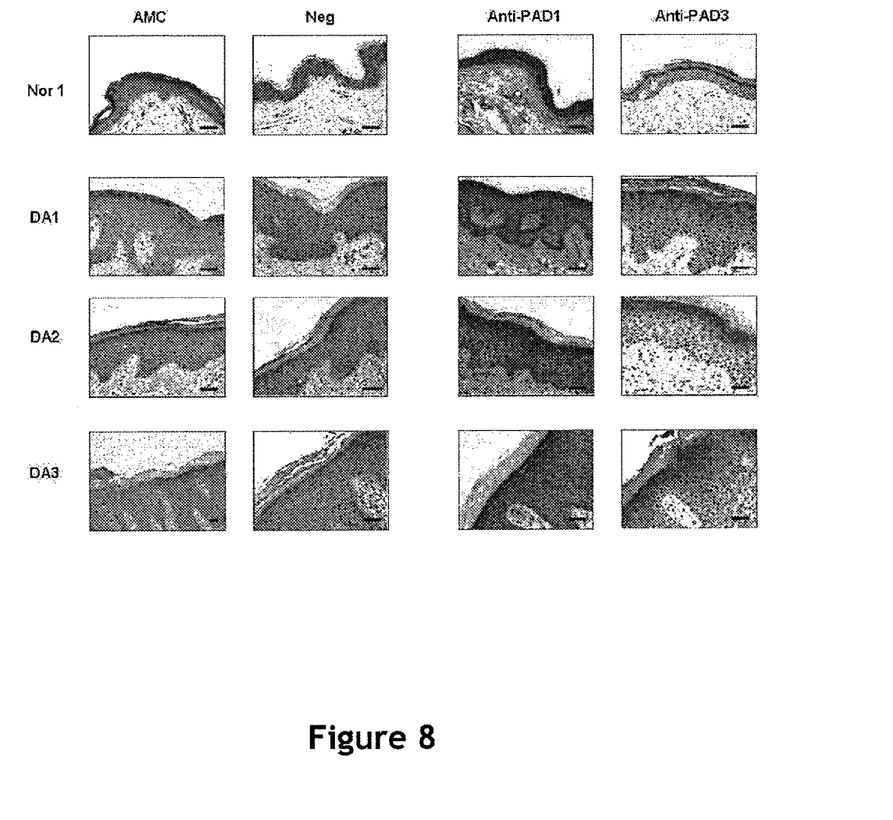
FIG. 8: PAD1, PAD3 and deiminated proteins analyzed by immunohistology on sections of normal human skin or skin of patients suffering from atopic dermatitis.

Results:

1. Decrease in Deiminated Proteins in the Epidermis of Patients Suffering from Atopic Dermatitis All of the samples that did not undergo chemical modification are negative. Skin samples from the control individuals exhibit very strong and continuous staining with the AMC antibody throughout the horny layer and on all the corneocyte layers. On the other hand, skin samples from patients suffering from atopic dermatitis exhibit clearly weaker and often discontinuous staining of the horny layer (see FIG. 8).

In conclusion, the deimination of proteins of the lesioned epidermis of patients suffering from atopic dermatitis is clearly reduced in comparison with the healthy controls.

2. Expression of PAD1 and 3 in the Epidermis of Patients Suffering from Atopic Dermatitis For all samples of atopic skin taken, PAD1 is detected in the cytoplasm of keratinocytes of all the living layers of the epidermis, with a higher intensity in the most differentiated keratinocytes. The same immunodetection profile is observed for the normal skin samples, as is well-known to persons skilled in the art. The intensity of staining obtained on atopic skin and on normal skin is the same.

In normal epidermis, PAD3 is detected mainly in the cytoplasm of granular keratinocytes, as is well-known to persons skilled in the art. In the atopic epidermis of all the patients, PAD3 is detected in the cytoplasm of several cell layers of the most differentiated keratinocytes. The staining intensity is most often equal to that of the staining of normal epidermis (see FIG. 8).

PAD1 and PAD3 thus are widely expressed in the epidermis of patients suffering from atopic dermatitis. It is thus not an absence of these enzymes which explains the reduction in the deimination of the proteins observed previously, but perhaps a lower activity.

D/ Increase in Deiminated Proteins of the Horny Layer after Treatment with a Gel Containing Acefylline.

Methods:

1. Reconstructed Epidermises

Reconstructed human epidermises 0.33 cm$^2$ in size were grown at the air-liquid interface for 14 days. 5 mg/cm$^2$ of pre-formulas containing the various active agents was then applied homogeneously to their surface using a brush. Triplicates were carried out for a treatment period of 24 hours at 37° C. The epidermises were then divided: half were frozen in Tissue Tek and then 6 μm cryo-sections were made for immunohistology; the other half were dry frozen at −80° C. for the preparation of total protein extracts before analysis by Western blot. Total proteins were extracted by boiling in sample buffer (0.175 M Tris-HCl pH 6.8; 12.5% beta-mercaptoethanol, 7.5% SDS, 25% glycerol) and separated by SDS-PAGE, in 4-15% gradient gels.

2. Detection of Deiminated Proteins by Immunohistology

The deiminated proteins were immunodetected as described above after incubation in modification buffer. Negative controls were prepared systematically by omitting the modification. After washing with water, the sections were incubated with AMC anti-citrulline antibody diluted to 1/1000. Finally, counter-staining was carried out with hematoxylin.

3. Detection of Deiminated Proteins by Western Blot

The protein extracts, clarified by centrifugation and separated by SDS-PAGE, were immunodetected by AMC anti-citrulline antibody as described above or by anti-actin antibody (Millipore, clone MAB1501). The immunodetection intensities were quantified as described above.

Results:

1. Increase in Deiminated Proteins in Reconstructed Epidermises Treated with Acefylline in the Form of Triethanolamine Salt or Sodium Salt.

Figure 9:
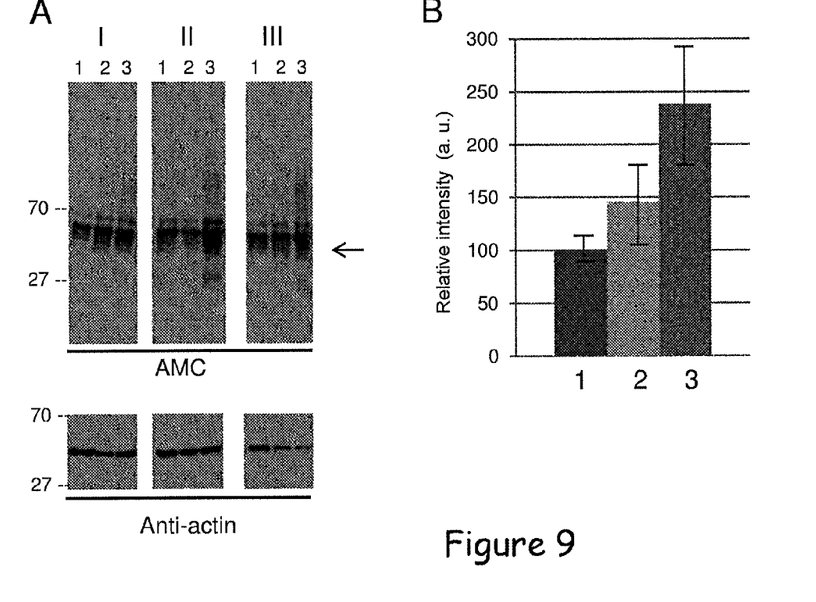
FIG. 9: Analysis by Western blot of deiminated proteins after topical application of acefylline in the form of triethanolamine salt or sodium salt, on the surface of reconstructed epidermises.

Deiminated proteins with an apparent molar mass between 90 and 30 kDa are detected in all the extracts (see FIG. 9A). One of them is filaggrin (arrow). The immunodetection intensity is greater (about 2.5 times) in the lanes corresponding to the epidermises treated with an aqueous gel containing acefylline in the form of triethanolamine salt or sodium salt than in those corresponding to the epidermises treated with aqueous gel alone (see FIGS. 9A and 9B).

2. Increase in Deiminated Proteins in the Horny Layer of Reconstructed Epidermises Treated with Acefylline in the Form of Sodium Salt.

Figure 10:
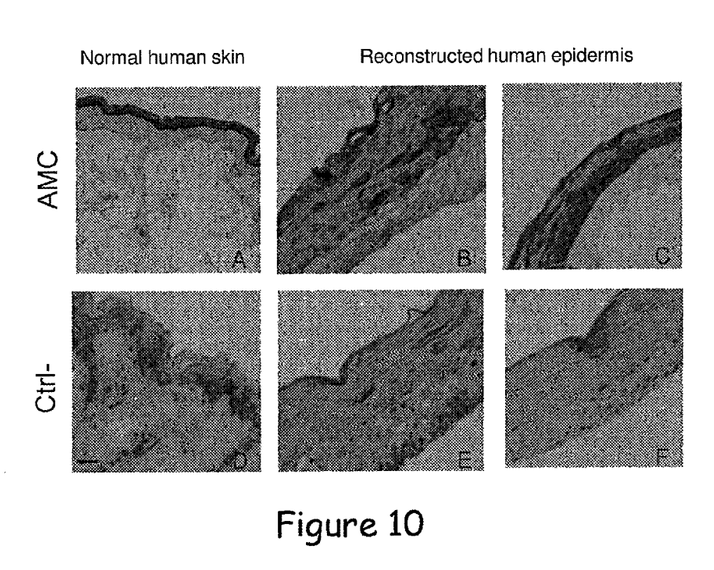
FIG. 10: Immunohistological analysis of deiminated proteins after topical application of acefylline in the form of sodium salt on the surface of reconstructed epidermises.

All samples that did not undergo chemical modification are negative (see FIGS. 10D, 10E and 10F). The samples of reconstructed epidermis exhibit with AMC antibody a discontinuous staining throughout the horny layer. The immunodetection intensity is stronger after treatment with acefylline in the form of sodium salt (see FIG. 10).

In conclusion, acefylline in salt form applied in an aqueous gel to the surface of the reconstructed epidermises increases the deimination of proteins of the horny layer and in particular of filaggrin.

E. Example of Preparation of an Aqueous Gel Containing 3% Acefylline in the Form of Sodium Salt

| INCI name | Function | % |
| --- | --- | --- |
| Acefylline | Active agent | 3 |
| Sodium hydroxide | Base | 0.51 |
| Hydroxyethylcellulose | Gelling agent | 1.5 |
| Phenoxyethanol | Preservative | 0.7 |
| Aqua (water) | Diluent | 94.29 |
| | | Addition 2% water |

Procedure

Step A: In water heated beforehand to 70° C., disperse acefylline with stirring (1300 rpm)+add NaOH: 70° C.

Step B: Add phenoxyethanol+slowly sprinkle natrosol with stirring (500 rpm) and then increase shearing.

Then B into A with stirring (1300 rpm for 10 minutes). Cool and homogenize (1 hour at 900 rpm)

Final pH=7.16

Macroscopic observations: thick, transparent, colorless gel.

EXAMPLES OF COMPOSITION

Several formulations according to the invention, in cream form, have the following compositions (the quantities are given in mass percentage in relation to the total weight of the composition).

Advantageously, the formulations according to the invention have between 0.5% and 3% of acefylline or a salt thereof, the percentage being adjusted according to the moisturizing capacity desired.

Example 1

| Name | % mass | Function |
| --- | --- | --- |
| Acefylline | 0.5 to 3 | Moisturizing agent |
| Glycerol | 15 | Humectant |
| Petroleum jelly | 8 | Emollient |
| Liquid paraffin | 2 | Emollient |
| Stearic acid | 1.5 | Emulsifier |
| Glycerol monostearate | 5 | Emulsifier |
| Cyclomethicone | 1.5 | Emollient |
| Dimethicone | 0.5 | Emollient |
| Polyethylene glycol 600 | 5.0 | Humectant |
| Triethanolamine | QS | Neutralizing agent pH = 6.5 |
| Propyl parahydroxybenzoate | QS | Preservative |
| Water | QSP 100.0 | |

Example 2

| Name | % mass | Function |
| --- | --- | --- |
| Acefylline | 0.1 to 1 | Moisturizing agent |
| Vegetable oil | 1.5 | Emollient |
| Cetearyl glucoside/Cetearyl alcohol | 5.0 | Emulsifier |
| Glyceryl stearate/PEG-100 stearate | 2.5 | Emulsifier |
| Liquid paraffin | 10.0 | Emollient |
| Shea butter | 1.0 | Emollient |
| PPG-15 STEARYL ETHER | 6.5 | Emollient |

-continued

| Name | % mass | Function |
| --- | --- | --- |
| Cyclomethicone | 6.0 | Emollient |
| Glycerin 99.5% | 7.0 | Humectant |
| Xanthan gum | 0.1 | Gelling agent and stabilizer |
| Polyacrylamide | 0.8 | Gelling agent and stabilizer |
| Preservatives | QS | Preservative |
| Butylhydroxytoluene | 0.01 | Antioxidant |
| NaOH | QS | Neutralizing agent pH = 6.5 |
| Fragrance | QS | Fragrance |
| Water | QSP 100.0 | |

The invention claimed is:

1. A method to treat an individual in need of skin moisturization comprising:
    administering to the individual an effective amount of a composition including acefylline or a salt thereof to moisturize the skin,
    wherein the composition further comprises at least one liquid fatty phase including at least one compound selected from oils and/or solvents of mineral, animal, vegetable or synthetic origin, containing carbon, hydrocarbon, fluorine and/or silicone, volatile or non-volatile, alone or in mixture.

2. The method according to claim 1, wherein moisturizing skin includes promotion of deimination of filaggrin in the epidermis.

3. The method according to claim 1, wherein moisturizing skin includes production of NMF (natural moisturizing factor) in the horny layer.

4. The method according to claim 1, wherein moisturizing skin includes moisturizing the epidermis, in particular the horny layer, to improve any form of dry skin, or to strengthen the epidermal barrier function and to prevent the signs of aging skin.

5. The method according to claim 1, wherein moisturizing skin includes promoting the natural production of trans-urocanic acid and to protect the skin from ultraviolet rays.

6. The method according to claim 1, wherein the composition further includes caffeine and/or theobromine.

7. The method according to claim 1, wherein the composition includes acefylline or a salt thereof represents at between 0.1% and 1% by weight of the total weight of the composition.

8. The method according to claim 1, wherein the composition includes acefylline at between 0.5% and 3% by weight of the total weight of the composition.

9. A method to treat an individual in need of skin moisturization comprising:
    administering to the individual an effective amount of a composition including acefylline or a salt thereof to moisturize the skin,
    wherein the composition excludes ethyl alcohol.

10. A method to treat an individual in need of skin moisturization comprising:
    administering to the individual an effective amount of a composition including acefylline or a salt thereof to moisturize the skin,
    wherein the composition further includes an emollient and a humectant.

11. The method according to claim 10, wherein the emollient is selected from petroleum jelly, liquid paraffin, cyclomethicone, dimethicone, vegetable oil, shea butter, and stearyl ether.

12. The method according to claim 11, wherein the humectant is selected from polyethylene glycol, glycerol, and glycerin.

13. The method according to claim 12, wherein the composition includes acefylline or a salt thereof represents at between 0.1% and 1% by weight of the total weight of the composition.

14. The method according to claim 10, wherein the composition includes acefylline at between 0.5% and 3% by weight of the total weight of the composition.

15. The method according to claim 10, wherein the composition further includes caffeine and/or theobromine.

* * * * *